United States Patent [19]
Alcott et al.

[11] Patent Number: 6,156,328
[45] Date of Patent: Dec. 5, 2000

[54] INSECTICIDE-CONTAINING FOAM SHEET AND PROCESS FOR THE PREPARATION THEREOF

[75] Inventors: Jeff M. Alcott; Brad Gougeon; James J. Kubiak, all of Midland, Mich.

[73] Assignee: The Dow Chemical Company, Midland, Mich.

[21] Appl. No.: 09/241,845

[22] Filed: Feb. 1, 1999

[51] Int. Cl.$^7$ .......................... A01N 25/34; A01N 25/00; C08J 9/00
[52] U.S. Cl. .......................... 424/405; 424/403; 424/404; 521/94; 521/142; 521/143; 521/146
[58] Field of Search .............................. 521/94; 424/405, 424/403, 404; 514/65

[56] References Cited

U.S. PATENT DOCUMENTS

| | | | |
|---|---|---|---|
| Re. 32,356 | 2/1987 | Cardarelli | 424/78 |
| 3,286,400 | 11/1966 | Gruenewaelder | 47/8 |
| 3,589,891 | 6/1971 | Mocette et al. | 71/94 |
| 4,247,498 | 1/1981 | Castro | 264/41 |
| 4,400,374 | 8/1983 | Cardarelli | 424/78 |
| 4,519,909 | 5/1985 | Castro | 210/500.2 |
| 4,636,257 | 1/1987 | Suh et al. | 521/79 |
| 5,147,481 | 9/1992 | Deblander | 156/71 |
| 5,149,726 | 9/1992 | Deblander | 521/143 |
| 5,173,535 | 12/1992 | Abrutyn | 525/54.3 |
| 5,194,323 | 3/1993 | Savoy | 428/305.5 |
| 5,224,315 | 7/1993 | Winter, IV | 52/309.8 |
| 5,270,108 | 12/1993 | Savoy | 428/305.5 |
| 5,373,674 | 12/1994 | Winter, IV | 52/309.9 |
| 5,549,869 | 8/1996 | Iwakawa | 422/40 |
| 5,598,677 | 2/1997 | Rehm, III | 52/407.1 |
| 5,695,870 | 12/1997 | Kelch et al. | 428/318.4 |
| 5,704,172 | 1/1998 | Gougeon et al. | 52/169.11 |

FOREIGN PATENT DOCUMENTS

| | | | |
|---|---|---|---|
| 10036549A2 | 2/1989 | Japan | C08J 9/228 |
| 2170211A | 7/1986 | United Kingdom | C08K 5/00 |

OTHER PUBLICATIONS

Derwent Abstract No. 83–742057/34 (Abstract of DE 3204847, published Aug. 18, 1983).
Derwent Abstact No. 86–098673/15 (Abstract of JP 61044934A, published Mar. 4, 1986).
Derwent Abstract No. 88–216722/31 (Abstract of JP 63152648A, published Jun. 25, 1988).
Derwent Abstract No. 89–065045/09 (Abstract of JP–01016864A, published Jan. 20, 1989).
Derwent Abstract No. 89–066013/09 (Abstract of JP–01019001A, publsihed Jan. 23, 1989).
Derwent Abstract No. 89–082549/11 (Abstract of JP 01036629A, published Feb. 7, 1989).
Derwent Abstract No. 89–367806/50 (Abstract of JP–01275822A, published Nov. 6, 1989).
Derwent Abstract No. 93–161986/20 (Abstract of JP 05092490, published Apr. 16, 1993).
Derwent Abstract No. 94–263647/32 (Abstract of WO 9416560–A1, published Aug. 4, 1984).
Derwent Abstract No. 95–009876 (Abstract of JP 06294165A, published Oct. 21, 1994).

*Primary Examiner*—Morton Foelak

[57] ABSTRACT

A polymer foam sheet having a thickness of at least 0.3 cm, an average cell size of at least 0.1 mm, and at least one pyrethrum compound dispersed in the polymer matrix, wherein the total amount of pyrethrum compounds in the sheet, based on the weight of the foam solids therein, is from 1 part per million (ppm) to 20,000 ppm.

36 Claims, No Drawings

INSECTICIDE-CONTAINING FOAM SHEET AND PROCESS FOR THE PREPARATION THEREOF

BACKGROUND OF THE INVENTION

This invention relates to polymeric foam structures sufficiently insect-repellent to deter insects from chewing through or nesting in the foam and affecting its physical properties.

Rigid and flexible polymeric foam products are used throughout the building construction industry as thermal insulation, protection boards, sill plate and closure gaskets, and expansion/contraction, seismic, isolation joint filler and vibration damping and cushioning materials. These polymeric foams do not provide nutritional value to attract and support insects, but an insect in search of food and shelter may attack them.

It is known to surface-treat construction materials with insecticides to kill insects that may come in contact with or ingest the treated surface material. These insecticide surface treatments typically leach out of the materials over time, or degrade in the presence of air, water, or light, thereby limiting their long-term efficacy. Further, despite the mortality of the initial insect attack, insects may continue the foraging or nesting attack until the insecticide surface treatment has been breached or efficacy lost. Once they have burrowed into the construction materials, insects can find protection from outside weather, nesting space and may be hidden from detection and further insecticide treatments. The resulting infestation by insects may destroy the physical properties of the foam for which it was selected and used.

SUMMARY OF THE INVENTION

In one aspect, this invention is a polymer foam sheet having a thickness of at least 0.3 cm, an average cell size of at least 0.1 mm, and at least one pyrethrum compound dispersed in the polymer matrix, wherein the total amount of pyrethrum compounds in the sheet, based on the weight of the foam solids therein, is from 1 part per million (ppm) to 20,000 ppm.

In another aspect, this invention is a process for making foam sheet that comprises extruding or molding a foamable polymer composition having at least one pyrethrum compound dispersed therein, wherein the total amount of pyrethrum compounds in the sheet, based on the weight of the foam solids therein, is from 1 part per million (ppm) to 20,000 ppm, under conditions sufficient to form a foam sheet having a thickness of at least 0.3 cm and an average cell size of at least 0.1 mm.

It has been discovered that the foam sheet and process of the invention provides a means to obtain foam sheet having a relatively long-lasting insect repellence and/or pesticidal activity throughout the sheet at a relatively low concentration of pyrethrum compound. This invention may also permit the process to make the foam sheet to be run under pressure, temperature, and foaming conditions which may be necessary to produce a foam sheet having a suitable density, R-value retention, uniformity, and surface appearance, particularly for an extrusion process, while the compounds retain a relatively high and long-lasting efficacy. Preferably, the compounds do not rapidly degrade, leach or elute out of the sheet while used in an insulation application. These and other advantages will be apparent from the description that follows.

DETAILED DESCRIPTION OF THE PREFERRED EMBODIMENTS

The term "sheet" as used herein means a substantially flat article having a thickness substantially smaller than its width or length, and includes article shapes also commonly referred to planks or boards. Preferably, the thickness of the sheet is at least ⅛-inch (0.3 cm), more preferably at least 0.5 cm, more preferably at least ¼ inch (0.63 cm), and most preferably at least ½ inch (1.2 cm); but is preferably no greater than 6 inches, more preferably no greater than 5 inches, and most preferably no greater than 4 inches; its length is preferably at least 24 inches, more preferably at least 36 inches, most preferably at least 48 inches; but is preferably no greater than 120 inches, more preferably no greater than 108 inches, and most preferably no greater than 96 inches. The width of the sheet is preferably at least 16 inches, more preferably at least 20 inches, most preferably at least 24 inches; but is preferably no greater than 60 inches, more preferably no greater than 54 inches, and most preferably no greater than 48 inches.

The term "pyrethrum" compound as used herein means pyrethrin compounds derived from chrysanthemum plants, or the same or similar compounds derived from other natural sources, and pyrethroid compounds manufactured synthetically. Specific examples of such compounds include, but are not imited to, deltamethrin, permethrin, cypermethrin, ifenthrin, cyfluthrin, cyhalothrin, tefluthrin, resmethrin, allethrin, kadethrin, sanmarton, fenvalerate, esfenvalerate, lambda-cyhalothrin, tralomethrin, fenpropathrin, tetramethrin, as well as mixtures thereof. These compounds may be extracted from plant sources or may be prepared by a suitable chemical process, and are commercially available from such sources as AgrEvo, Zeneca, Bayer, FMC Corporation, and Aldrich Chemical. Preferably, the compound is a pyrethroid compound selected from deltamethrin, permethrin, bifenthrin, and mixtures thereof.

The pyrethrum family of compounds have very effective surface contact insect repellence, which is key to the prevention of insect attack to any foam products which contains them. The thermal and chemical stability and structure of pyrethrum compounds is key to their suitability in plastic manufacturing processes. After manufacture, many pyrethrum compounds remain encapsulated in the foam plastic resin because of their chemical structure and relatively low vapor pressure. As a result, the pyrethrum compounds provide long-term protection against insect borings that could affect the physical properties of the foam. The concentration of pyrethrum compounds in the foam that provides the desired efficacy depends on the specific material used and the targeted insect. In general, the pyrethrum compounds are preferably employed in a cumulative amount, based on the weight of the foam solids, of at least 2 ppm, more preferably at least 5 ppm, more preferably at least 20 ppm, more preferably at least 50 ppm, and most preferably at least 200 ppm; but preferably no greater than 10,000 ppm, more preferably no greater than 5,000 ppm, and more preferably no greater than 2,000 ppm and most preferably no greater than 1,000 ppm, depending on commercial and technical needs. The term "foam solids" as used herein means the weight of the foam, exclusive of any blowing agent or other gases that are contained in the cells of the foam.

In the foam sheet of the invention, the pyrethrum compounds are dispersed in the polymer matrix of the sheet. This means that when a section of the foam sheet having a thickness of less than twice the average size of the cells (so that the section has few closed cells, even if the sheet from which the section is cut is primarily a closed-cell foam) is contacted with a solvent for the compounds which is a non-solvent for the polymer, the major portion of the compounds in the section do not dissolve in the solvent because they are trapped in the polymer matrix instead of residing at an open cell/polymer interface, or other space in the section of the sheet where the solvent may contact the compound.

The pyrethrum compounds may be included in the foam by direct addition of a neat, formulated or encapsulated material, or by adding a polymer concentrate containing such material, to a polymer foam formulation prior to foaming in a polymeric foam process. The compounds are preferably dispersed in the polymer matrix by thoroughly mixing them with the polymer at a temperature above its glass transition temperature before the polymer is contacted with a gaseous blowing agent under conditions suitable to make the foam sheet. The compounds may also be added during the polymerization process for the creation of expandable polystyrene molding beads.

Pyrethrum compounds have adequate thermal and chemical stability to be used in foam plastic processes. Foam plastics containing these materials have relatively long-term efficacy of insect repellence and mortality. The plastic resin structure of the foam provides long-term environmental protection of the pyrethrum compounds, thereby maintaining their presence and chemical structure. The chemical structure and physical properties of pyrethrum compounds minimize the elution and leaching of these compounds from the foam plastic structure. Functional properties of foam plastic products are not significantly affected by concentrations of pyrethrum compounds that are needed for insect repellence and mortality efficacy.

The term "foamable polymer composition" as used herein means a thermoplastic polymer-containing precursor material for the process to make the foam sheet. Such compositions may comprise polymers that may be combined with a blowing agent prior to extrusion into a suitable shape, or polymers that may be combined with a blowing agent to make foamable beads that then foam during a pre-expansion and molding process. A variety of polymers are known to be useful in foam-making processes including polyolefins and alkenyl aromatic polymers. Suitable polyolefins include polyethylene, polypropylene, polyethylene terephthalate and polyvinyl chloride. Suitable alkenyl aromatic polymers include polystyrene and copolymers of styrene and other monomers. Suitable polyethylenes include those of high, medium, low, linear low, and ultra low density types.

The foamable polymer composition preferably comprises an alkenyl aromatic polymer material. The alkenyl aromatic polymer material may be comprised solely of one or more alkenyl aromatic homopolymers, one or more alkenyl aromatic copolymers, a blend of one or more of each of alkenyl aromatic homopolymers and copolymers, or blends of any of the foregoing with a non-alkenyl aromatic polymer. Regardless of composition, the alkenyl aromatic polymer material comprises greater than 50 and preferably greater than 70 weight percent alkenyl aromatic monomeric units. Most preferably, the alkenyl aromatic polymer material is comprised entirely of alkenyl aromatic monomeric units.

Suitable alkenyl aromatic polymers include those derived from alkenyl aromatic compounds such as the solid homopolymer of styrene, a-methylstyrene, o-methylstyrene, m-methylstyrene, p-methylstyrene, ar-ethylstyrene, ar-vinylxylene, ar-chlorostyrene, vinyl benzene, vinyl toluene, and bromostyrene or ar-bromostyrene; the solid copolymers of one or more of such alkenyl aromatic compounds and minor amounts of monoethylenically unsaturated compounds such as C2-6 alkyl acids and esters, ionomeric derivatives, and $C_{4-6}$ dienes may be copolymerized with alkenyl aromatic compounds. Examples of copolymerizable compounds include acrylic acid, methacrylic acid, ethacrylic acid, maleic acid, itaconic acid, acrylonitrile, citraconic anhydride, itaconic anhydride, maleic anhydride, methyl acrylate, ethyl acrylate, isobutyl acrylate, n-butyl acrylate, methyl methacrylate, vinyl acetate and butadiene. A preferred alkenyl aromatic polymer is polystyrene. Preferred structures comprise substantially (i.e., greater than 95 percent) polystyrene. most preferably, all of the polymer in the foam sheet is polystyrene.

The foam sheet of the invention is preferably a rigid extruded polystyrene or expanded polystyrene bead foam board (bead board). The most preferred rigid insulating foam is extruded polystyrene. Extruded polystyrene foams are preferred because they provide relatively high compressive strength and modulus, are relatively impermeable to water and water vapor, and are capable of retaining insulating cell gas for long periods of time.

In the preparation of the foam sheet, the blowing agent may be added to the resin in any convenient manner. In an extrusion process, the blowing agent mixture is pumped into heat plastified alkenyl aromatic resin and admixed therewith prior to extrusion through a die to form foam. The blowing agent may be admixed and pumped as a combination stream into the heat plastified resin, or they may be supplied as separate streams. Adequate mixing of the blowing agents into the heat plastified resin is required in order to obtain a product of desirable uniformity. Such mixing may be accomplished by a variety of means including dynamic mixers such as extruders, so-called static mixers or interfacial surface generators, such as are utilized in U.S. Pat. Nos. 3,751,377 and 3,817,669.

The blowing agent or mixture of blowing agents is preferably utilized in an amount of at least 3 pph (parts by weight per one hundred parts by weight of polymer), more preferably at least 5 pph, most preferably at least 7 pph; but is preferably no greater than 25 pph, more preferably no greater than 20 pph, and most preferably no greater than 18 pph. Examples of suitable blowing agents include hydrocarbon, hydrochlorofluorocarbon, hydrofluorocarbon, halocarbon, carbon dioxide and other suitable physical and chemical blowing agents as needed in the foam processes.

An example of an extrusion process to make foam articles utilizing a mixture of blowing agents is described in U.S. Pat. No. 4,636,527, which is hereby incorporated by reference in its entirety, in which a foam sheet defining a plurality of closed noninterconnecting gas-containing primary cells is prepared by a method comprising heat plastifying an alkenyl aromatic polymer, mixing the polymer with a volatile fluid foaming agent under a pressure sufficiently high that foaming is prevented, reducing the temperature of the mixture to a temperature such that when pressure is removed therefrom, a foam of desirable quality is obtained. Another foam-making process is shown and described in U.S. Pat. No. 2,669,751, wherein the volatile fluid foaming agent is injected into a heat-plastified polymer stream within an extruder. From the extruder the heat-plastified gel is passed into a mixer. The heat-plastified gel from the extruder is fed into the inlet end of the mixer and discharged from the outlet end, the flow being in a generally axial direction. From the mixer, the gel passes through coolers such as are described in U.S. Pat. No. 2,669,751 and from the coolers to a die which extrudes a generally rectangular board. A generally similar extrusion system and a preferred extrusion system are shown in U.S. Pat. No. 3,966,381.

Other processes for making extruded foams are described in U.S. Pat. Nos. 2,409,910; 2,515,250; 2,669,751; 2,848, 428; 2,928,130; 3,121,130; 3,121,911; 3,770,688; 3,815,674; 3,960,792; 3,966,381; 4,085,073; 4,146,563; 4,229,396; 4,302,910; 4,421,866; 4,438,224; 4,454,086 and 4,486,550. If an extrusion process is used, the extruded foam formulation typically reaches a maximum temperature of at least 210° C. and possibly of at least 240° C., and a pressure of at least 900 psi and possibly of at least 1900 psi.

If the foam sheet is comprised of polystyrene, it is preferably a closed-cell foam having an closed cell content of 90 percent to 100 percent according to ASTM D2856-94. Preferably, the closed cell content is at least 95 percent, more preferably at least 97 percent. Processes for making such foam are seen in U.S. Pat. No. 5,434,195, which is incorporated herein by reference. The polystyrene foam sheet preferably has a density of at least 9.6 kg/m$^3$ (kilograms per cubic meter), more preferably at least 17.6 kg/m$^3$, most preferably at least 21.6 kg/m$^3$; but is preferably no greater than 64 kg/m$^3$, more preferably no greater than 40 kg/m$^3$, and most preferably no greater than 32 kg/m$^3$, according to ASTM D-1622-93.

If the foam sheet is comprised of polyethylene or polypropylene, the foam may be open cell, closed cell, contain both open and closed cells, or may be formed as a plurality of coalesced strands or profiles depending on the needs of the application. Processes for making such foam are seen, for example, in U.S. Pat. Nos. 5,348,795; 5,527,573; 5,567,742; and 4,824,720, which are incorporated herein by reference. The polyethylene foam sheet preferably has a density of at least 8 kg/m$^3$ (kilograms per cubic meter) (0.5 lb/ft$^3$), more preferably at least 16 kg/m$^3$, most preferably at least 24 kg/m$^3$; but preferably no greater than 160 kg/m$^3$, more preferably no greater than 48 kg/m$^3$, according to ASTM D-3575.

Various additives may be incorporated in the present foam structure such as inorganic fillers, pigments, stabilizers, antioxidants, acid scavengers, ultraviolet absorbers, flame retardants, processing aids, dispersion aids, extrusion aids, and the like. In addition, other additives with insecticidal repellent and/or synergistic properties, such as piperonyl butoxide, may be added to the foamable polymer composition prior to foaming, or may be applied to the exterior portion of the foam sheet in a post-treatment process.

In the preparation of foams in accordance with the present invention, it is often desirable to add a nucleating agent to reduce the primary cell size. Preferred nucleating agents include inorganic substances such as calcium carbonate, calcium silicate, indigo, talc, clay, titanium dioxide, silica, calcium stearate, diatomaceous earth, mixtures of citric acid and sodium bicarbonate, and the like. The amount of nucleating agent employed may range from about 0.01 to about 5 parts by weight per hundred parts by weight of a polymer resin. The preferred range is from 0.1 to about 3 parts by weight. The average cell size is preferably at least 0.01 mm, more preferably at least 0.1 mm, most preferably at least 0.15 mm; but is preferably no greater than 5 mm, more preferably no greater than 3 mm, and most preferably no greater than 1 mm, as may be measured by ASTM D-3576-94.

The foam sheets may be prepared to any suitable size. A common size for commercial foam sheet is a 4 foot by 50 foot sheet that is sold fan-folded at 2-foot intervals, or rolled up. Common sheet thicknesses range from 0.3–0.95 cm (⅛–⅜ inch). The foam sheet of the invention is preferably provided in the form of a relatively thin, rectangular board. Common board sizes are about 2 feet by 8 feet (61 centimeters (cm) by 244 cm) and 4 feet by 8 feet (122 cm by 244 cm) in width and length. If desired, one or both faces of the foam sheet may be grooved to facilitate post treatment with additional quantities of insecticide/termiticide. The sheet may also be grooved to facilitate the drainage of water induced by hydrostatic pressure in the backfill as described, for example, in U.S. Pat. Nos. 4,309,855, 4,704,048, and 5,056,281. Additionally, if desired, one or both faces of the foam sheet may have a film laminated thereto, to increase the strength of the sheet at the interface.

The foam sheet of the invention preferably has adequate compressive strength, density, R-value retention, and water absorption properties, uniformity, and surface appearance, to make it useful for a variety of applications, including exterior building insulation. The foam sheet contains an amount of pyrethrum compound that is effective to repel or kill at least one type of insect which would otherwise chew or burrow through polymer foam board, especially termites. The insecticidal or insect repellent properties of the board may be tested by any suitable method such as, for example, by inducing the insect(s) to crawl across, chew, or burrow through the board by placing a strong-smelling food in a position relative to the insect so that the insect can smell the food and must crawl across, or chew or burrow through the board to reach the food. To determine the insecticidal or insect-repellent properties of the inner portion of the board, it may be desirable to first slice off the outer portions of the board to remove the exterior foam cell layers.

ILLUSTRATIVE EMBODIMENTS

The following examples illustrate the invention, but are not intended to limit it in any way.

EXAMPLES 1–3

Styrene polymer foams are prepared according to the following process with an additive feed of a styrene resin masterbatch containing 2 percent by weight of deltamethrin, permethrin, and bifenthrin. A styrene polymer foam is prepared utilizing a 2½-inch diameter extruder that feeds a dynamic mixer, generally of the configuration disclosed in U.S. Pat. No. 2,669,751. The dynamic mixer discharge is passed through multiple heat exchangers of the variety shown in U.S. Pat. No. 3,014,702. The discharge from the heat exchangers is in turn passed through a plurality of interfacial surface generators or static mixers of the type shown in U.S. Pat. No. 3,583,678. The discharge from the static mixers is passed to a slot die. Foam is discharged from the slot die at a rate of 200 pounds per hour.

Acceptable foam products with deltamethrin, permethrin, and bifenthrin levels of approximately 200 ppm and 1000 ppm by weight of resin are obtained by mixing the masterbatch with sufficient additional amounts of polystyrene to obtain a resin feed having the desired concentration of pyrethroid.

We is claimed is:

1. A polymer foam sheet having a thickness of at least 0.3 cm, an average cell size of at least 0.1 mm, and at least one pyrethrum compound dispersed in the polymer matrix,
   wherein the total amount of pyrethrum compounds in the sheet, based on the weight of the foam solids therein, is from 1 ppm to 20,000 ppm.

2. The polymer foam sheet of claim 1 wherein the total amount of pyrethrum compounds in the sheet, based on the weight of the foam solids therein, is at least 20 ppm.

3. The polymer foam sheet of claim 1 wherein the total amount of pyrethrum compounds in the sheet, based on the weight of the foam solids therein, is at least 50 ppm.

4. The polymer foam sheet of claim 1 wherein the total amount of pyrethrum compounds in the sheet, based on the weight of the foam solids therein, is at least 200 ppm.

5. The polymer foam sheet of claim 4 that is comprised of polystyrene, and has a density of at least 9.6 kg/m$^3$.

6. The polymer foam sheet of claim 5 that has a closed cell content of at least 90 percent.

7. The polymer foam sheet of claim 6 that has a closed cell content of at least 95 percent.

8. The polymer foam sheet of claim 7 that has a thickness of at least 1.2 cm.

9. The polymer foam sheet of claim 4 that is comprised of polyethylene, has a density of at least 16 kg/m$^3$, and a closed cell content of at least 70 percent.

10. The polymer foam sheet of claim 1 that has a thickness of at least 0.5 cm.

11. A polymer foam sheet having a thickness of at least 0.3 cm, an average cell size of at least 0.1 mm, and at least one pyrethrum compound selected from deltamethrin, permethrin, cypermethrin, bifenthrin, cyfluthrin, cyhalothrin, tefluthrin, resmethrin, allethrin, kadethrin, fenvalerate, esfenvalerate, lambda-cyhalothrin, tralomethrin, fenpropathrin, tetramethrin, sanmarton, and mixtures thereof, dispersed in the polymer matrix, wherein the total amount of the pyrethrum compounds in the sheet, based on the weight of the foam solids therein, is from 1 ppm to 20,000 ppm.

12. The polymer foam sheet of claim 11 wherein the total amount of pyrethrum compounds in the sheet, based on the weight of the foam solids therein, is at least 20 ppm.

13. The polymer foam sheet of claim 11 wherein the total amount of pyrethrum compounds in the sheet, based on the weight of the foam solids therein, is at least 50 ppm.

14. The polymer foam sheet of claim 11 wherein the total amount of pyrethrum compounds in the sheet, based on the weight of the foam solids therein, is at least 200 ppm.

15. The polymer foam sheet of claim 14 that is comprised of polystyrene, and has a density of at least 9.6 kg/m$^3$.

16. The polymer foam sheet of claim 15 that has a closed cell content of at least 90 percent.

17. The polymer foam sheet of claim 16 that has a closed cell content of at least 95 percent.

18. The polymer foam sheet of claim 17 that has a thickness of at least 1.2 cm.

19. The polymer foam sheet of claim 14 that is comprised of polyethylene, has a density of at least 16 kg/m$^3$, and a closed cell content of at least 70 percent.

20. The polymer foam sheet of claim 19 that has a thickness of at least 0.5 cm.

21. The polymer foam sheet of claim 11 wherein the pyrethrum compound is deltamethrin, permethrin, bifenthrin, or a mixture thereof.

22. The polymer foam sheet of claim 21 wherein the total amount of pyrethrum compounds in the sheet, based on the weight of the foam solids therein, is at least 20 ppm.

23. The polymer foam sheet of claim 21 wherein the total amount of pyrethrum compounds in the sheet, based on the weight of the foam solids therein, is at least 50 ppm.

24. The polymer foam sheet of claim 21 wherein the total amount of pyrethrum compounds in the sheet, based on the weight of the foam solids therein, is at least 200 ppm.

25. The polymer foam sheet of claim 22 that is comprised of polystyrene and has a density of at least 9.6 kg/m$^3$.

26. The polymer foam sheet of claim 25 that has a closed cell content of at least 90 percent.

27. The polymer foam sheet of claim 25 that has a closed cell content of at least 95 percent.

28. The polymer foam sheet of claim 25 that has a thickness of at least 1.2 cm.

29. The polymer foam sheet of claim 24 that is comprised of polyethylene, has a density of at least 16 kg/m$^3$, and a closed cell content of at least 70 percent.

30. The polymer foam sheet of claim 29 that has a thickness of at least 0.5 cm.

31. A process for making a foam sheet that comprises extruding or molding a foamable polymer composition having at least one pyrethrum compound dispersed therein, wherein the total amount of pyrethrum compounds in the sheet, based on the weight of the foam solids therein, is from 1 part per million (ppm) to 20,000 ppm, under conditions sufficient to form a foam sheet having a thickness of at least 0.3 cm and an average cell size of at least 0.1 mm.

32. The process of claim 31 wherein the pyrethrum compound is deltamethrin, permethrin, cypermethrin, bifenthrin, cyfluthrin, cyhalothrin, tefluthrin, resmethrin, allethrin, kadethrin, fenvalerate, esfenvalerate, lambda-cyhalothrin, tralomethrin, fenpropathrin, tetramethrin, sanmarton, or a mixture thereof.

33. The process of claim 32 wherein the pyrethrum compound is deltamethrin, permethrin, bifenthrin, or a mixture thereof.

34. The process of claim 33 wherein the pyrethrum compound is exposed to a temperature of at least 210° C. and a pressure of at least 900 psi during said extrusion or molding of the foam sheet.

35. The process of claim 34 wherein the pyrethrum compound is exposed to a temperature of at least 240° C. during said extrusion or molding of the foam sheet.

36. The process of claim 35 wherein the pyrethrum compound is exposed to a pressure of at least 1900 psi during said extrusion or molding of the foam sheet.

* * * * *